Figure 1:
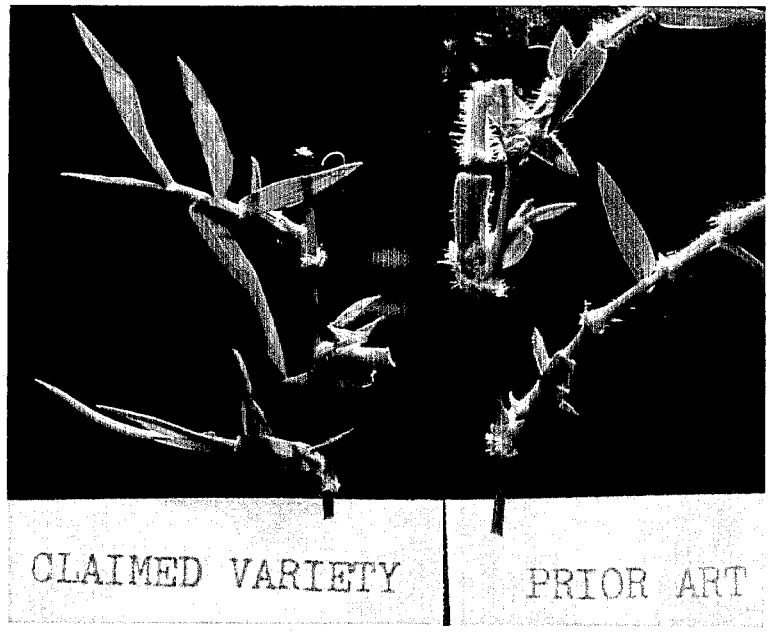

United States Patent [19]

Whiting

[11] Plant 5,194

[45] Feb. 21, 1984

[54] DIGITARIA DIDACTYLA GRASS PLANT

[75] Inventor: Hubert F. Whiting, Fallbrook, Calif.

[73] Assignee: AMFAC Garden Perry's Inc., Ventura, Calif.

[21] Appl. No.: 432,977

[22] Filed: Dec. 15, 1982

[51] Int. Cl.[3] ..... A01H 5/00

[52] U.S. Cl. ..... Plt./88

[58] Field of Search ..... Plt./88

*Primary Examiner*—Bagwill Robert E.

[57] ABSTRACT

I disclose that my herein invention of a new variety of Digitaria Didactyla grass plant was discovered by me through my cross-pollinating selected varieties of Digitaria Didactyla grass plant then through asexual repropagation selected the new and distinct variety of Digitaria Didactyla which produces an excellent turfgrass of superior moderate bluish-green color as defined in the ISCC-NBS centroid color chart; the anthers of the new variety Digitaria Didactyla are dark purple as defined in the ISCC-NBS centroid color chart; the stigmas of the new variety of Digitaria Didactyla are strong reddish-purple as defined in the ISCC-NBS centroid color chart; the new variety of Digitaria is glabrous on the sheath and in between the internode and has a more open texture.

4 Drawing Figures

The present invention and discovery relates to a new and distinct variety of Digitaria Didactyla grass plant which was discovered by me through cross-pollination of collected varieties of Digitaria Didactyla grass plants. This cross-pollination was done by me at Indio, Calif., about 34 degrees north latitude. I harvested seeds from this cross-pollination of the selected varieties of Digitaria Didactyla grass plants and planted these seeds out in germinating trays. Shortly after the seeds germinated I transplanted each separate seedling into one-gallon containers. There were 331 of these seedlings planted out by me in this way. As these seedlings grew and matured, I selected the most desirable for turfgrass potential. This left 105 seedlings. These 105 seedlings were then each individually broken up by me into small pieces of stolons, then I planted these small pieces of stolons into the soil in an area that was three-feet square. When this process was completed, I had 105 individual seedlings planted in 105 three square plots, all asexually transplanted by me. The location of this transplanting was at Fallbrook, Calif. Once these 105 three-foot square plots became established through the spreading of the planted stolons, I formed a turf-grass surface through regular mowing. I again made selections from the 105 plots. The selections I made this time were again individually transplanted by me asexually by breaking sufficient stolon material of each separate selection to further replant the now 23 selections into larger individual separate plots of ten feet by eight feet. Once these larger plots became established through the spreading of the planted stolons I formed a turfgrass surface through regular mowing. I again made selections from these 23 plots. The new claimed variety of Digitaria Didactyla grass plant is one of those selections, and its designation is D-40. This new selected variety of Digitaria Didactyla grass plant spread by stolons to produce an excellent turfgrass surface when regularly mown. During the following seasons I observed an earlier spring green color of a more open texture with a much deeper blue-green color than the closest known variety of Digitaria Didactyla grass plant. During the continued asexual reproduction by stolons I have confirmed that the above-described characteristics are transmitted through succeeding propagations, and have confirmed that the new variety of Digitaria Didactyla grass plant has the following unique combination of characteristics: The new and distinct claimed variety of Digitaria Didactyla grass plant is illustrated in the accompanying color photographs, with photographs of the closest known Digitaria Didactyla grass plant. The most noticeable variations between the two grasses are the deep bluish-green color of the new claimed variety, and a more open upright turfgrass surface, and the new claimed variety has anthers of dark purple color with stigmas of strong reddish-purple color. The new claimed variety is glabrous except for a few hairs around the stolon node.

IN THE DRAWINGS

FIG. 1 is a photograph of two pieces of stolons taken from the same test area, one piece is of the new and distinct variety of Digitaria Didactyla grass plant, the other piece of stolon is of the closest-known variety of Digitaria Didactyla grass plant (identified by prior art). This photograph shows the new claimed variety glabrous, except for a few hairs on the internodes, compared to the closest-known variety (identified by prior art) which is dense pubescent on the sheath and between the internodes.

Figure 2:
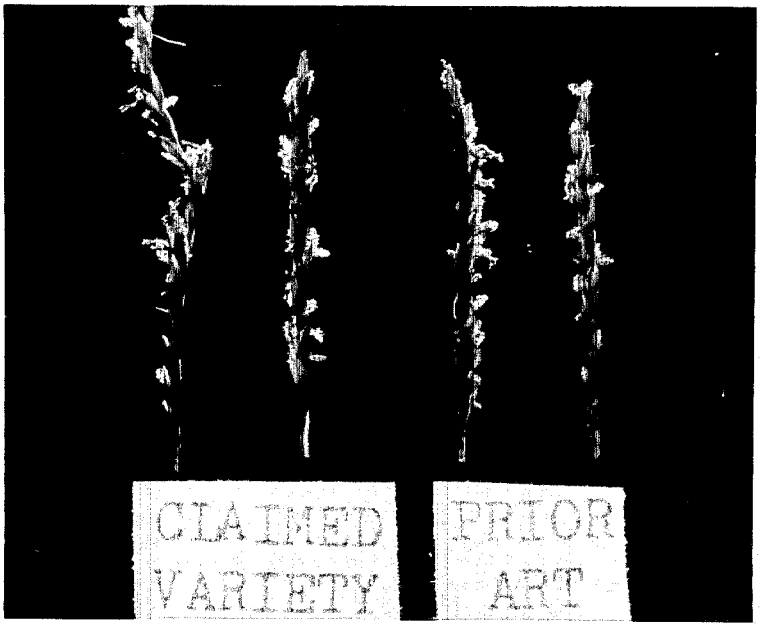

FIG. 2 is a photograph of spikes taken from the same test area of the new claimed variety of Digitaria Didactyla grass plant, and the closest-known variety of Digitaria Didactyla grass plant (identified by prior art). This photograph shows the dark purple colored anthers, Color Number 224.d.p. of the ISCC-NBS Centroid color chart, and the strong reddish-purple colored stigmas, Color Number 237.s.rp of the ISCC-NBS Centroid color chart of the new claimed variety of Digitaria Didactyla grass plant, compared to the closest-known variety of Digitaria Didactyla grass plant, which has light yellowish-brown colored anthers, Color Number 76.1.ybr of the ISCC-NBS Centroid color chart, with deep purplish-red colored stigmas, Color Number 256.deep pr of the ISCC-NBS Centroid color chart.

Figure 3:
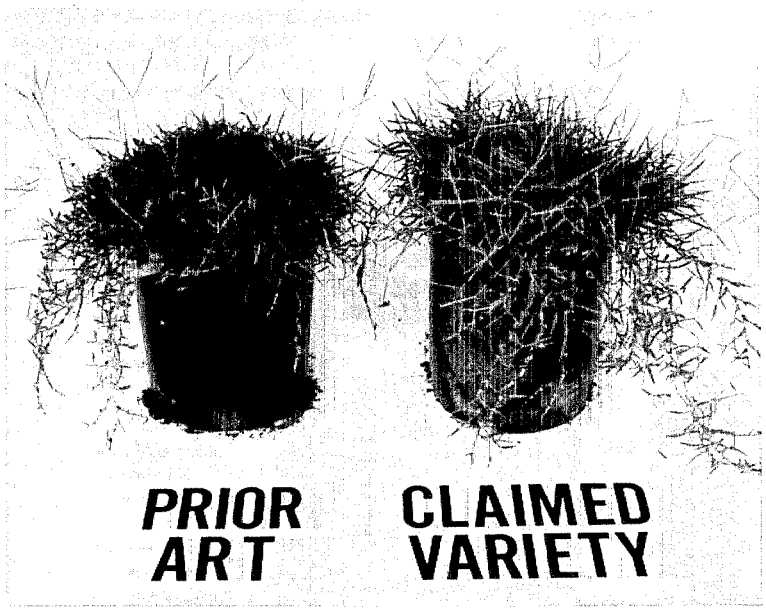

FIG. 3 is a photograph showing side views of pots containing the new and distinct variety of Digitaria Didactyla grass plant and the closest-known variety of Digitaria Didactyla grass plant (identified by prior art), both grasses being taken from the same test area and potted at the same time and further showing both grasses being unmown or uncut. This photograph shows a more upright growth habit of the new claimed variety of Digitaria Didactyla grass plant compared to the closest known variety of Digitaria Didactyla grass plant (identified by prior art) which has a lower more dense growth habit.

Figure 4:
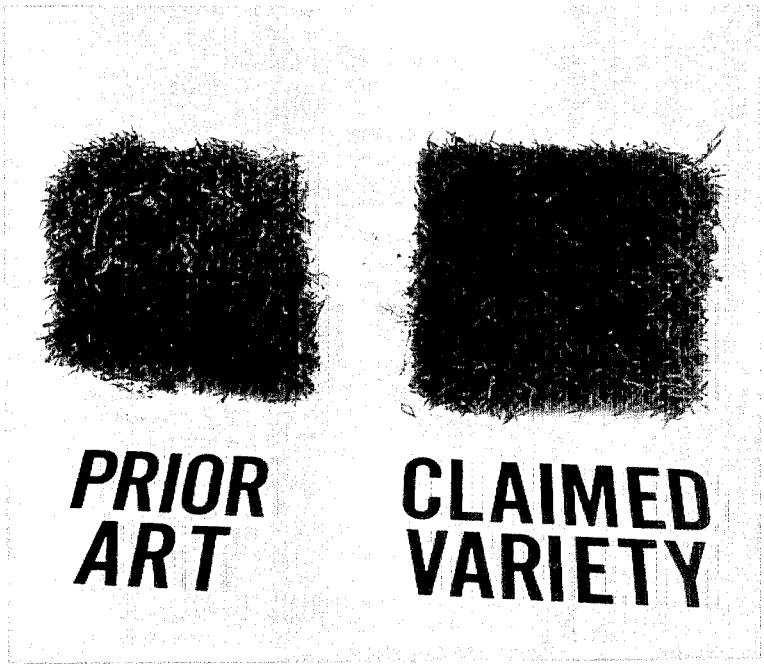

FIG. 4 is a photograph of a top view of sod pieces taken from the same test area of the new claimed variety of Digitaria Didactyla grass plant and the closest-known variety of Digitaria Didactyla grass plant (identified by prior art), which sod pieces have been subject to the same mowing conditions at virtually the same time with identical maintenance practices. This photograph shows the more open texture with a moderate bluish-green color, Color Number 164.m.bg of the ISCC-NBS centroid color chart, compared to the closest-known variety of Digitaria Didactyla grass plant (identified by prior art) which is more dense with a moderate yellowish-green color, Color Number 136.m.yg of the ISCC-NBS centroid color chart.

A detailed description of the new and distinct variety of Digitaria Didactyla grass plant is:

(a) An attractive moderate bluish-green color, Color Number 164.m.bg of the ISCC-NBS centroid color chart;
(b) The grass is low growing erect in habit;
(c) The grass spreads by stolons and rhizomes forming a dense uniform surface with an extensive root system;
(d) Culms vary in height from 8–35 cm;
(e) Leaves rolled in bud shoot;
(f) The blade is V-shaped in cross-section keeled and gradually tapering to an acute point;
(g) The first mature leaf is 3–3.5 millimeters in width and 25–80 millimeters in length;
(h) The leaf blade is glabrous except at the base of the leaf close to the ligule where 3–4 hairs are present;
(i) The ligule is membranous acute and medium in height;
(j) Auricles are absent;
(k) The collar is narrow;
(l) The sheath is glabrous split with margins overlapping;
(m) The entire plant is glabrous except on the upper leaf surface near the ligule and on top of the sheath around the internodes;
(n) The internodal spaces on the stolons are 1–5 centimeters and on the culms 1–6 centimeters;
(o) Inflorescence consists of 2–3 spikes at the top of the main stem deflexed at maturity from 25–45 millimeters long;
(p) The spiklets are glabrous in two rows 2–3 millimeters long blunt at their base, pointed at their tips, born singly on short branches and glumes are present; the spiklet contains stigmas of strong reddish-purple, Color Number 237.s.rp of the ISCC-NBS centroid color chart, and anthers of dark purple, Color Number 224.d.p. of the ISCC-NBS centroid color chart.

Description of the closest-known variety of the species, by comparison the closest-known variety of the species is a lower growing erect in habit; culms vary in height from 5–25 centimeters in length; the first mature leaf 3–3.5 millimeters in width, 25–75 millimeters in length; the blade is glabrous except near the ligule where a few hairs are present; the ligule is membranous acute and medium in height. The sheath is split pubescent very dense pubescent around the node area. The spiklet contains light yellowish-brown colored anthers, Color Number 76.1.ybr of the ISCC-NBS centroid color chart with deep purplish-red colored stigmas, Color Number 256.deep pr of the ISCC-NBS centroid color chart.

Having now described the new and distinct variety of Digitaria Didactyla grass plant which I have discovered and asexually reproduced, I claim:

1. A new variety of Digitaria Didactyla grass plant herein shown and described by a moderate bluish-green color as defined by the ISCC-NBS centroid color chart; this new variety has an earlier spring green color of a more open and upright growth habit with stolons that are glabrous except for a few hairs around the nodes; the anthers are a dark purple color as defined by the ISCC-NBS centroid color chart; the stigmas are of a strong reddish-purple color as defined by the ISCC-NBS centroid color chart.

* * * * *